United States Patent [19]
Davis

[11] Patent Number: 4,957,486
[45] Date of Patent: Sep. 18, 1990

[54] RECTAL-STOMAL INSERT APPARATUS AND METHOD

[76] Inventor: Emsley A. Davis, P.O. Box 942, McCamey, Tex. 79752

[21] Appl. No.: 416,064

[22] Filed: Oct. 2, 1989

[51] Int. Cl.$^5$ .......................................... A61M 29/00
[52] U.S. Cl. ...................................... 604/96; 604/43; 604/104; 604/328; 128/4; 606/197
[58] Field of Search .................................. 604/27-28, 604/39, 41, 43, 45, 93, 96-105, 200, 275, 277-278, 328; 128/4; 606/108, 197; 600/29-32

[56] References Cited

U.S. PATENT DOCUMENTS

| | | | |
|---|---|---|---|
| 2,494,088 | 1/1950 | Dulity | 604/39 |
| 2,922,415 | 1/1960 | Campagna | 128/4 |
| 3,421,509 | 1/1969 | Fiore | 604/200 X |
| 3,771,522 | 11/1973 | Waysilk et al. | 604/39 X |
| 4,117,847 | 10/1978 | Clayton | 604/328 X |
| 4,573,965 | 3/1986 | Russo | 604/30 |
| 4,721,508 | 1/1988 | Burton | 604/338 |
| 4,776,845 | 10/1988 | Davis | 604/96 |

OTHER PUBLICATIONS

Photocopies of actual endotracheal tube and its package.

Primary Examiner—C. Fred Rosenbaum
Assistant Examiner—C. Maglione
Attorney, Agent, or Firm—Arthur F. Zobal; Geoffrey A. Mantooth

[57] ABSTRACT

An apparatus for use during examination of the colon of a patient includes an insertion member and a tube member. The insertion member, which occludes the opening into the colon, has first and second channels extending between inner and outer ends. The first channel receives a colonoscope, while the second channel receives the tube member. Seals are provided to prevent air leakage from inside of the colon out through the two channels. The tube member provides a conduit into the colon that is independent of the colonoscope. The tube member has an inside channel for receiving colonoscopic tools. There is an inflatable balloon at the inner end of the tube member, for blunting the tube member inner end. An inflation channel extending between the balloon and the tube member outer end allows the balloon to be remotely inflated. With the insertion member in place in the opening, the tube member is inserted into the colon, via the second channel. The tube member provides a conduit for directing tools to a point of interest inside the colon, which tools are used to remove and retrieve tissue samples of the colon walls.

11 Claims, 2 Drawing Sheets

RECTAL-STOMAL INSERT APPARATUS AND METHOD

FIELD OF THE INVENTION

The present invention relates to medical devices, particularly those devices that can be inserted into an opening of a patient.

BACKGROUND OF THE INVENTION

Davis, U.S. Pat. No. 4,776,845 describes an apparatus that is designed for insertion into the rectum or stoma of a human being. The inventor in Davis U.S. Pat. No. 4,776,845 is the same as the inventor of the present invention. The rectal-stomal insert apparatus described in U.S. Pat. No. 4,776,845 is used during a colonoscopy, wherein a surgeon conducts a visual examination of a patient's colon by the use of remote instrumentation. For the examination procedure, the surgeon utilizes a colonoscope and the rectal-stomal insert apparatus. The colonoscope has a sensing tube that is inserted into the colon. The sensing tube has optical means to provide illumination and viewing of the inside of the colon, and insufflation means for inflating the colon. Inflation of the colon makes the examination easier and reduces the risk of injury.

The rectal-stomal insert apparatus is inserted into the rectum or stoma of a patient before the examination to provide a seal, whereby air pressure for inflating the colon and fecal material are prevented from leaking out. The rectal-stomal insert apparatus is provided with an instrument channel for receiving the colonoscope sensing tube and a suction channel for allowing suctioning of fecal material from the colon. The colonoscope sensing tube is inserted into the colon through the instrument channel, wherein the examination can commence.

During a typical examination, the surgeon takes tissue samples of the colon for later laboratory analysis. In the prior art, the surgeon retrieves a tissue sample by inserting a snaring tool into a small (2 mm in diameter) passageway in the colonoscope sensing tube. The snaring tool is pushed through the colonoscope passageway to the end of the sensing tube where it is used to severe a tissue sample from the colon wall. The snaring tool is removed from the colonoscope and a basket retrieval tool is inserted into the colonscope passageway. The basket tool is used to capture the tissue sample. The surgeon removes the colonoscope with the basket tool to retrieve the specimen from the colon. The surgeon then reinserts the colonoscope and resumes the examination of the colon.

When the colonoscope is reinserted, the surgeon tries to resume the examination where he left off, i.e. at the location in the colon where the tissue sample was taken. However, in practice, it is very difficult to relocate the end of the sensing tube in the same spot in the colon from which it was withdrawn. As a result, the surgeon must either reinspect some of the colon, or search for the spot where the specimen was taken. Either way, the process of reinserting the colonoscope is time consuming. Another time consuming aspect of the prior art is the physical removal and reinsertion of the colonoscope every time a tissue sample is taken. What is needed is an apparatus that will allow the removal of tissue during a colonoscopy without having to remove the colonoscope.

SUMMARY OF THE INVENTION

It is an object of the present invention to provide an apparatus and method that will allow the removal of tissue samples during a colonoscopy without having to remove the colonoscope.

It is a further object of the present invention to provide an apparatus and method that will allow the removal of tissue samples during a colonoscopy, which apparatus can be used in conjunction with the rectal-stomal insert apparatus.

The apparatus includes an insertion member and a tube means. The insertion member occludes the opening into the colon, preventing leakage of air pressure or fecal material, while allowing the insertion of the colonoscope and the tube means. The tube means provides a conduit into the colon that is independent of the colonoscope. Thus, the interior of the colon can be accessed, and material can be removed, without disturbing the colonoscope.

The insertion member has an inner end to be inserted first into the opening of a colon of a patient, an opposite outer end, and an exterior surface. The insertion member includes a first channel extending therethrough between the outer and inner ends for receiving instrumentation and a second channel formed separate from the first channel which extends through the insertion member between the outer and inner ends. Occlusion means is located around the insertion member for forming a seal between the exterior surface and the perimeter of the opening of the patient. The tube means has inner and outer ends. The tube means inner end is insertable into the second channel of the insertion member such that the tube means inner end projects beyond the insertion member inner end. The tube means has an inside channel for receiving tool means for use in the colon. The inside channel extends between the tube means inner and outer ends. The tool means may be inserted into the inside channel from the tube means outer end such that the tool means projects beyond said tube means inner end. The tube means inner end has inflatable balloon means for blunting the tube means inner end to allow safe insertion of the tube means inner end into the colon. The tube means has an inflating channel for inflating and deflating the balloon means. The inflating channel extends between the tube means outer end to the tube means inner end. The inner end of the inflating channel communicates with the interior of the balloon means. The outer end of the inflating channel is adapted to couple to inflation means for inflating the balloon means. The inflating channel is separate from the inside channel of the tube means.

In one aspect, the apparatus includes seal means for sealing the tube means inside channel from gas leakage. The seal means allows the passage of the tool means. A second seal means seals the second channel around the tube means. The second seal means allows the tube means to be slid inside of the second channel.

In another aspect the inflating channel outer end comprises valve means for retaining fluid in said balloon means, and monitor balloon means for monitoring the inflation level of the balloon means.

In still another aspect, the balloon means encompass the tube means inner end while allowing the inside channel to communicate with the exterior of the tube means at the tube means inner end portion.

The method of the present invention includes the steps of providing an insertion member having inner and outer ends. The insertion member is capable of occluding an opening in the colon and has first and second channels. The insertion member is inserted into the colon opening so as to occlude the opening. Instrumentation is inserted into the colon through the first channel. The instrumentation is used to examine the colon. Tissue samples may be removed from the colon without removal of the colonscope from the colon by use of a tube means, which has inner and outer ends. The tube means inner end has inflatable balloon means for blunting the tube means inner end when the balloon means is inflated. The tube means has an inside channel extending between its inner and outer ends. The tube means inner end is inserted into the colon through the second channel of the insertion member. The balloon means is inflated and the tube means inner end is extended further into the colon to the location of the tissue sample. Tool means is inserted into the colon through the inside channel from the tube means outer end. The tool means are used to obtain a tissue sample and remove the tissue sample from the colon.

DESCRIPTION OF PREFERRED EMBODIMENT

Figure 1:
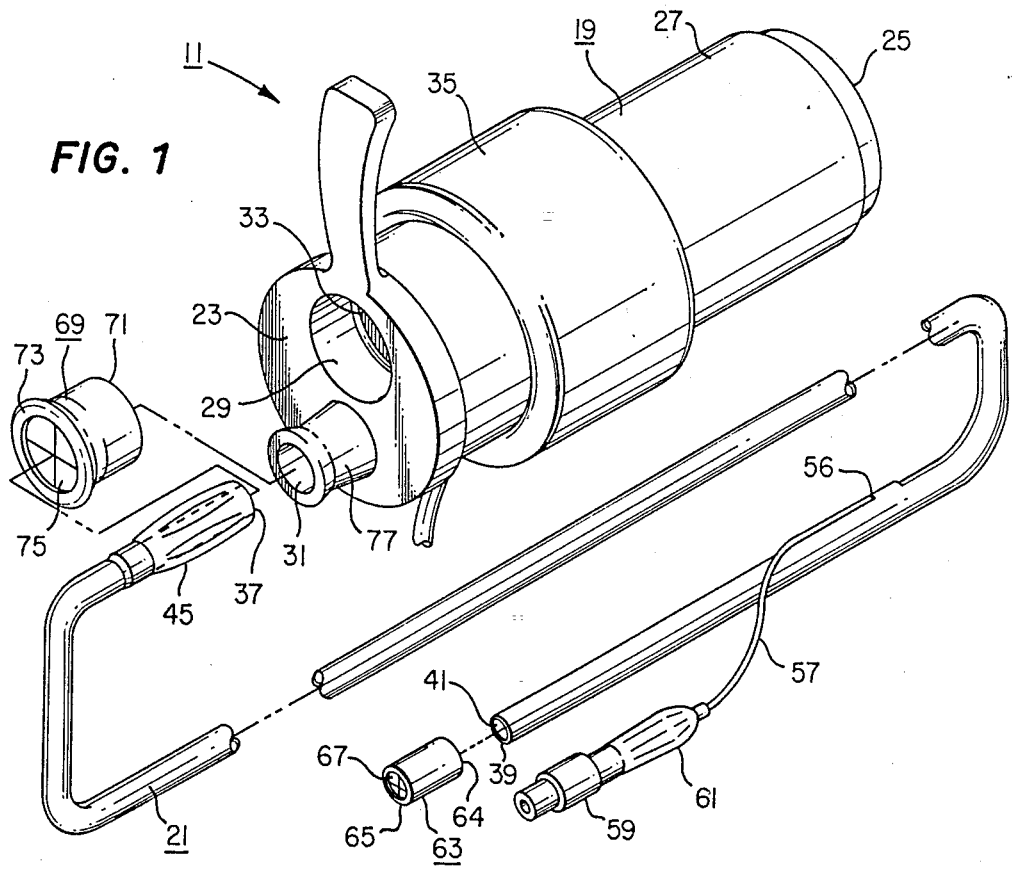
FIG. 1 is an isometric view of the apparatus of the present invention, in accordance with a preferred embodiment.

In FIG. 1 there is shown the apparatus 11 of the present invention, in accordance with a preferred embodiment. The apparatus 11 is used in conjunction with a colonoscope 13 (see FIGS. 3 and 4 which show the colonoscope sensing tube schematically) to inspect the colon 15 of a human being. During a colonoscopy, a surgeon inserts a colonoscope into a patient's colon, by way of the patient's anus 17 or stoma (in those patients lacking a rectal opening). The apparatus 11 is used to occlude the opening 17 through which the colonoscope is inserted, thereby preventing the inadvertent discharge of fecal material during the examination. In addition, the colon is inflated with air provided by the colonoscope; use of the apparatus prevents uncontrolled leakage of air through the opening, thereby preventing the collapse of the colon.

The surgeon uses the colonoscope to examine the interior of the colon. If the surgeon finds any suspicious looking tissue, he will remove a tissue sample for later analysis. With the apparatus of the present invention, the surgeon can remove a tissue sample, while maintaining the integrity of the occlusion at the opening 17. In addition, the surgeon can remove a tissue sample while maintaining the position of the colonoscope, so that the examination can proceed from that same location, once the tissue sample is removed.

The apparatus of the present invention includes an insertion member 19 and a tube member 21.

The insertion member 19 has an outer end 23, an inner end 25, and a cylindrical exterior surface 27. First and second channels 29, 31 extend through the insertion member 19 between the outer and inner ends 23, 25. The first channel 29 receives the sensing tube of the colonoscope 13, and is provided with a seal 33 for sealing around the colonoscope. An inflatable occlusion member 35 is provided around the exterior surface 27 of the insertion member 19. The occlusion member 35 inflates to provide a seal between the insertion member 19 and the tissue wall of the opening 17 into which the insertion member is placed. The insertion member 19 is described in more detail in Davis U.S. Pat. No. 4,776,845, which is hereby incorporated by reference into this disclosure.

The tube member 21 has inner and outer ends 37, 39 and an inside channel 41 that extends between the ends. The outside diameter of the tube member 21 is such that the tube member can be inserted into the second channel 31 of the insertion member 19. The diameter of the inside channel 41 is such that colonoscopic tools such as a basket 43 (see FIG. 4), a snare, or forceps can be inserted into the inside channel. The length of the tube member is such that it can be inserted into the length of the colon from the anus.

Figure 2:
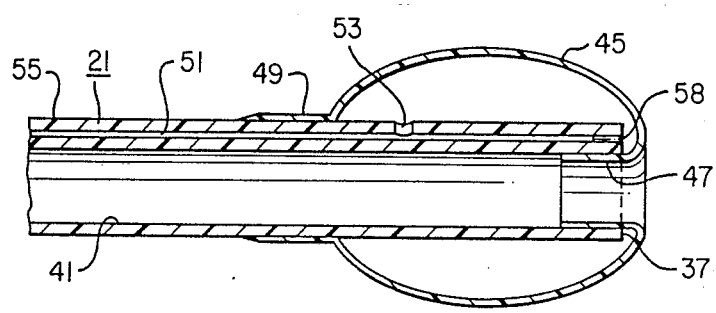
FIG. 2 is an enlarged longitudinal cross-sectional view of the inner end of the tube member, showing the balloon inflated.

At the inner end 37 of the tube member 21 is an inflatable balloon 45 (see FIG. 2). When inflated, the balloon 45 blunts the inner end 37 of the tube member 21, thereby reducing the risk of injury to the colon 15 when the tube member is inserted into the colon. The balloon 45 has an inner end portion 47 and an outer end portion 49. The balloon outer end portion 49 is secured with a suitable adhesive to the outside of the diameter of the tube member 21 a short distance away from the tube member inner end 37. The balloon inner end portion 47 is secured by a suitable adhesive to the tube member inside channel 41 at the inner end of the tube member. Thus, the inner end 37 of the tube member 21 is completely covered by the balloon 45, while the inside channel 41 of the tube member communicates with the exterior at the inner end portion of the tube member. When the balloon 45 is deflated, its outside diameter decreases so that the inner end portion of the tube member 21 can be inserted through the second channel 31 of the insert member 19. When the balloon 45 is inflated, the maximum outside diameter of the balloon is located about midway between the balloon outer end and the balloon inner tip. The inflated balloon provides a blunted tube member end. In an alternative configuration, the balloon wall thickness can be varied to control the shape of the balloon. For example, the balloon thickness at the inner end portion can be made thinner than at the outer end and central portions so that the diameter of the inner end portion of the balloon will be larger than is shown in FIG. 2.

The balloon 45 is inflated by inflation means at the outer end of the tube member. An inflating passage connects the inflation means to the interior of the balloon 45. The inflating passage is made up of an inflating channel 51, located within the tube member wall 55, and an external inflating tube 57. The inflating channel 51 is separate from the inside channel 41, being entirely confined within the tube member wall 55. The inflating channel 51 extends between the inner and outer ends 37, 39 of the tube member 21. At each end of the tube member 21, the inflating channel is occluded with a plug 58. As shown in FIG. 2, the tube member wall 55 has, in its outside portion, an opening 53 near the tube member inner end 37, so as to provide communication between the inflation channel 51 and the interior of the balloon 45. At a point near the tube member outer end 39 one end 56 of the inflating tube 57 is coupled to the tube member wall 55 so as to allow communication between the inflating channel 51 and the interior passage of the inflating tube 57. The outer end of the inflating tube 57 has a conventional fitting 59. The fitting has a check valve for allowing fluid flow inwardly so as to inflate the balloon, while preventing the exit of the fluid. The fitting 59 receives the end of a syringe (not shown). The fitting 59 has a monitoring balloon 61, the interior of which communicates with the inflation channel 51 via the tube 57. Thus, the inflation status of the balloon 45 can be checked with the monitoring balloon 61.

The tube member 21 is provided, at its outer end 39, a first cap seal 63 that fits around the outside diameter of the tube member. The cap seal 63, which blocks the flow of air, has an open end 64 and a closed end 65. The open end 64 receives the tube member 21. The closed end 65 has a circular rubber seal element 67, which has a cruciate split to allow the passage of colonoscopic tools.

There is also provided a second cap seal 69. The second cap seal 69 also has open and closed ends 71, 73. The open end 71 receives a fitting 77 on the insertion member 19, around the second channel 31. The closed end 73 has a circular rubber seal element 75 which has a cruciate split to receive the tube member 21. The tube member 21 can be moved (by sliding) relative to the second cap seal 69 and the second channel fitting 77.

In the preferred embodiment, the insertion member 19 is made of hard plastic, the tube member 21 is made of flexible plastic, and the tube member balloon 45 and the occlusion member 35 are made of a rubber or elastomeric material.

Figure 3:
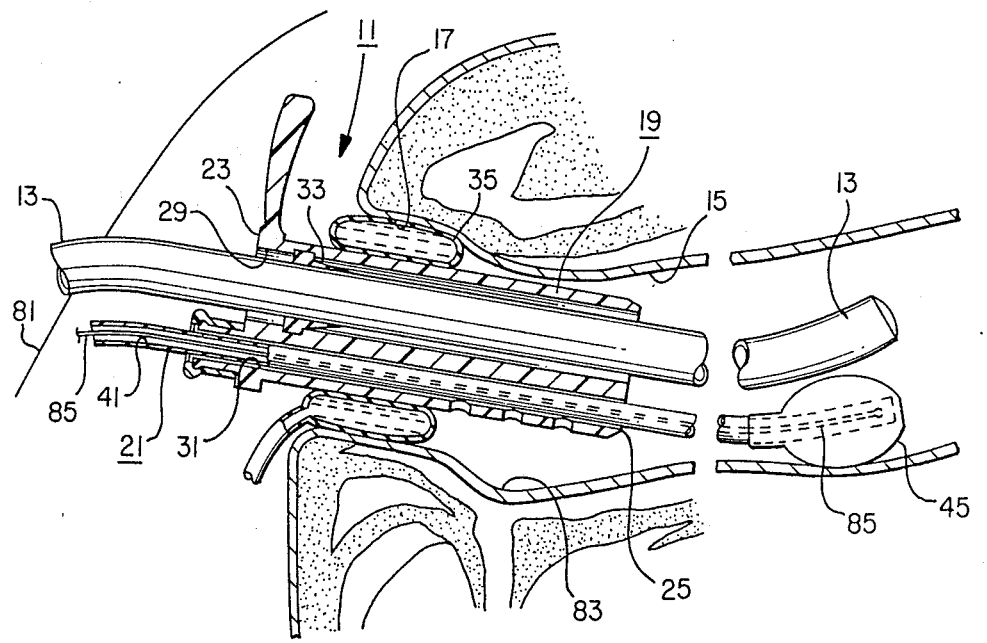
FIG. 3 is a cross-sectional view showing the apparatus inserted into the rectal area of a patient.
Figure 4:
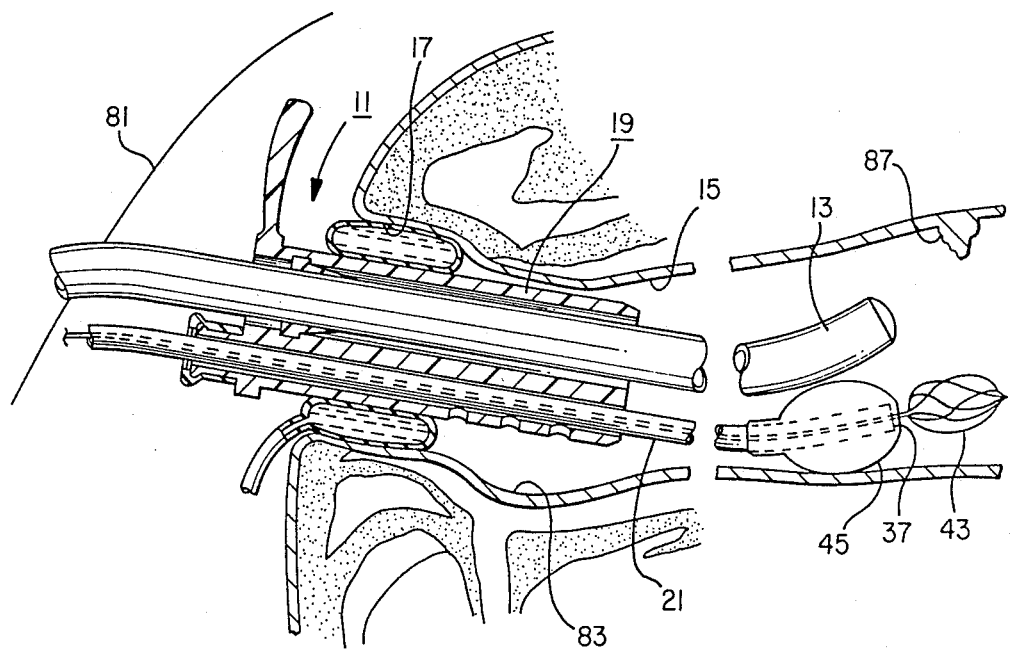
FIG. 4 is a cross-sectional view, similar to FIG. 3, with a basket retrieval tool inserted into the apparatus of the present invention.

Referring to FIGS. 3 and 4, the use of the apparatus 11 in the present invention will now be described. The apparatus is sterilized in accordance with conventional practice before being put into use. In FIGS. 3 and 4, there are shown posterior portions of a human patient 79, including the buttocks 81, the anus 17, and the rectum 83 (which is part of the colon).

The anus 17, which is the opening to the colon 15, is occluded by the use of the insertion member 19. The insertion member 19 is inserted, inner end 25 first, into the anorectal area 17, 83 of the patient. Insertion aids (not shown) are used to ease the insertion of the insertion member and prevent patient injury. Once the insertion member 19 is properly positioned, the occlusion member 35 is inflated with either a saline solution or air. The occlusion member 35 provides a seal between the insertion member 19 and the anal tissue.

The sensing tube of the colonoscope 13 is inserted into the first channel 29, through the outer end 23 of the insertion member 19. The sensing tube 13 has optical sensing means for transmitting visual images back to the surgeon. The sensing tube also has insufflation means for providing air to expand the colon. The sensing tube 13 is pushed into the colon via the first channel 29, wherein the examination can begin. During the examination, suction means (not shown) can be attached to the second channel fitting 77 to suction fecal material from the rectum 83. The second channel 31, if not being used for suction, is sealed with the second cap seal 69 to prevent the uncontrolled leakage of air out of the colon 15.

During the examination, the surgeon may wish to remove tissue samples in order to perform a biopsy. To remove a tissue sample, without removing the colonoscope, the surgeon inserts the inner end 37 of the tube member 21 into the second channel 31, through the split seal 75 of the second cap seal 69. The balloon 45 is deflated during insertion through the insertion member 19. The tube member 21 is pushed inward until the balloon 45 extends beyond the insertion member inner end 25 and is located in the rectum 83. The tube member 21 can be marked with markings (not shown) indicating the distance from the inner end 37 in order to assist in determining when the balloon has cleared the second channel.

The balloon 45 is then inflated with either air or a saline solution to blunt the inner end 37. A syringe (not shown) is coupled to the fitting 59 to pump in fluid. The inflation status of the balloon 45 is checked by observing the monitoring balloon 61. When the monitoring balloon is fully inflated, the balloon 45 is fully inflated.

Then, a stylet 85, or other suitable guide wire, is inserted into the tube member 21, through the first cap seal 63, to provide stiffness. The tube member 21 is pushed further into the colon 13, until the inner end 37 reaches the end of the sensing tube 13. The balloon 45 assists the tube member inner end in traversing the bends in the colon 15. The stylet 85 is then removed from the tube member 21. A snaring tool (not shown) is inserted into the colon either through a small instrument channel in the colonoscope or through the inside channel 41 of the tube member 21. The snaring tool, which is conventional, is used to sever a sample of tissue 87 from the colon wall. The snaring tool may be removed from the colon after the tissue sample is severed from the colon wall. Alternatively, the snaring tool may be left in place in the colon, particularly if the snaring tool is located in the colonoscope instrument channel. A conventional basket tool 43 is collapsed to reduce its outside diameter and then inserted into the tube member 21. The basket 43 is inserted until the basket protrudes from the inner end of the tube member, wherein the basket expands to its operational configuration. The basket tool 43 is manipulated from its outer end until the tissue sample 87 is captured inside of the basket. If the tissue sample is small enough, it may be removed by removing the basket through the inside channel 41 and leaving the tube member 21 in place in the colon 15. However, if the tissue sample is too large to fit through the inside channel, it can be removed by removing the tube member together with the basket. When the basket 43 reaches the rectum 83, the tissue sample can be deposited in the rectum, wherein the sample is retrieved from the rectum after the removal of the tube member, the colonoscope and the insertion member from the patient. An anoscope can be used to retrieve the tissue sample from the rectum 93.

Thus, when using the apparatus of the present invention, tissue samples can be removed from the colon while leaving the colonoscope in place, thereby eliminating the need to remove and then reposition the colonoscope inside of the colon. The insertion member occludes the anal opening, while the tube member provides a large diameter conduit, separate from the colonoscope, for use in directing tools to the tissue site of interest of the colon.

With the apparatus of the present invention, large tissue samples can be removed from the colon. With the prior art, tissue samples having a diameter of about 2 mm were the largest samples that could be removed. But with the apparatus of the present invention, tissue samples having larger diameters on the order of 1–3 cm.

can be removed. The larger tissue samples enable a more accurate laboratory analysis.

Once the tissue sample has been deposited, the tube member and the basket can be used to retrieve additional tissue samples. When the tube member is pulled out towards the rectum, the balloon 45 may be deflated. The balloon is deflated by squeezing the fitting 59, to open the check valve and allow the fluid to escape from the balloon.

The first and second cap seals 63, 69 provide air tight seals in and around the tube member 21. Thus, with the first and second cap seals 63, 69, the occlusion member 35 and the first channel seal 33, the anal opening is sealed against air pressure leakage.

Other tools, in addition to a snaring tool and a basket tool can be used in conjunction with the apparatus. For example, forceps can be inserted into the tube member to remove tissue. A coagulator to stop internal bleeding in the colon can also be inserted. Or, the tube member can be used as a conduit for introducing copious amounts of irrigation fluid to a specific point in the colon. Irrigation is useful to remove debris and blood. In addition, two or more tools can be introduced into the colon simultaneously by way of the tube member inside channel 41.

The foregoing disclosure and the showings made in the drawings are merely illustrative of the principles of this invention and are not to be interpreted in a limiting sense.

I claim:

1. An apparatus for insertion into an opening of a colon of a patient, comprising:
   (a) an insertion member having an inner end to be inserted first into the opening, an opposite outer end, and an exterior surface;
   (b) said insertion member comprising a first channel extending therethrough between said outer and inner ends for receiving instrumentation, and a second channel formed separate from said first channel extending through said insertion member between said outer and inner ends;
   (c) occlusion means located around said insertion member for forming a seal between said exterior surface and the perimeter of said opening of the patient;
   (d) tube means having inner and outer ends, said tube means inner end being insertable into said second channel of said insertion member such that said tube means inner end projects beyond said insertion member inner end;
   (e) said tube means having an inside channel for receiving tool means for use in said colon, said inside channel extending between said tube means inner and outer ends, wherein said tool means may be inserted into said inside channel from said tube means outer end such that said tool means projects beyond said tube means inner end;
   (f) said tube means inner end having inflatable balloon means for blunting said tube means inner end to allow safe insertion of said tube means inner end into said colon;
   (g) said tube means having an inflating channel for inflating and deflating said balloon means, said inflating channel extending between said tube means outer end to said tube means inner end, the inner end of said inflating channel communicating with the interior of said balloon means, the outer end of said inflating channel being adapted to receive inflation means for inflating said balloon means, said inflating channel being separate from said inside channel of said tube means.

2. The apparatus of claim 1 wherein said tube means further comprises seal means for sealing said tube means inside channel from fluid leakage from said colon, said seal means allowing the passage of said tool means.

3. The apparatus of claim 2 wherein said seal means is a first seal means, further comprising second seal means for sealing said second channel around said tube means, said second seal means allowing said tube means to be slid inside of said second channel.

4. The apparatus of claim 3 wherein said inflating channel outer end comprises valve means for retaining fluid in said balloon means, and monitor balloon means for monitoring the inflation level of said balloon means, the interior of said monitor balloon means communicating with the interior of said balloon means.

5. The apparatus of claim 4 wherein said balloon means encompasses said tube means inner end while allowing said inside channel to communicate with the exterior of said tube means at said tube means inner end portion.

6. The apparatus of claim 1 further comprising seal means for sealing said insertion member second channel around said tube means, said seal means allowing said tube means to be slid inside of said second channel.

7. The apparatus of claim 1 wherein said balloon means encompasses said tube means inner end while allowing said inside channel to communicate with the exterior of said tube means at said tube means inner end portion.

8. An apparatus for insertion into an opening of a colon of a patient, comprising:
   (a) an insertion member having an inner end to be inserted first into the opening, an opposite outer end, and an exterior surface;
   (b) said insertion member comprising a first channel extending therethrough between said outer and inner ends for receiving instrumentation, and a second channel formed separate from said first channel extending through said insertion member between said outer and inner ends;
   (c) occlusion means located around said insertion member for forming a seal between said exterior surface and the perimeter of said opening of the patient;
   (d) a tube member having inner and outer ends, said tube member having an inside channel extending between said tube member inner and outer ends, said tube member having a length between its inner and outer ends so that the tube member can be inserted into the length of the colon from said opening;
   (e) said tube member having an outside diameter that allows the insertion of said tube member into said second channel of said insertion member, said tube member being slidable within said second channel;
   (f) said tube member inside channel having a diameter that allows the insertion therein of tool means for use in said colon, wherein said tool means are slidable within said inside channel when inserted therein;
   (g) said tube member having inflatable balloon means at its inner end, said balloon means blunting the inner end of said tube member when inflated, said balloon means encompassing said tube member inner end, said tube member inner end being insertable into said second channel when said balloon means is deflated, said tube member having an inflating passage extending between said tube member outer and inner ends, said inflating passage communicating with the interior of said balloon means while being separate from said inside channel, said inflating passage outer end being adapted to receive inflation means;

(h) cap seal means having an open end and a closed end, said open end for receiving said tube member outer end, said closed end having first seal means, said first seal means for providing a seal in said inside channel while allowing said tool means to be slidable therethrough;

(i) second seal means for sealing said second channel around said tube member, said second seal means allowing said tube member to slide in said second channel.

9. A method of accessing the interior of a colon of a patient during a colonscopy, comprising the steps of:

(a) providing an insertion member having inner and outer ends, said insertion member capable of occluding an opening into the colon, said insertion member having first and second channels;

(b) inserting said insertion member into the colon opening so as to occlude said opening;

(c) inserting instrumentation into said colon through said first channel of said insertion member, and examining said colon with said instrumentation;

(d) providing conduit means having inner and outer ends, said conduit means inner end having inflatable balloon means for blunting said conduit means inner end when said balloon means is inflated, said conduit means having an inside channel extending between its inner and outer ends;

(e) inserting said conduit means inner end into said colon through said second channel of said insertion member;

(f) inflating said balloon means and extending said conduit means inner end further into said colon to the desired location;

(g) accessing the interior of said colon through said inside channel of said conduit means.

10. A method of removing a tissue sample from the inside of a colon of a patient, comprising the steps of:

(a) providing an insertion member having inner and outer ends, said insertion member capable of occluding an opening into the colon, said insertion member having first and second channels;

(b) inserting said insertion member into the colon opening so as to occlude said opening;

(c) inserting instrumentation into said colon through said first channel of said insertion member, and locating with said instrumentation a tissue sample to be removed from said colon;

(d) providing tube means having inner and outer ends, said tube means inner end having inflatable balloon means for blunting said tube means inner end when said balloon means is inflated, said tube means having an inside channel extending between its inner and outer ends;

(e) inserting said tube means inner end into colon through said second channel of said insertion member;

(f) inflating said balloon means and extending said tube means inner end further into said colon to the location of said tissue sample;

(g) inserting tool means for removing said tissue sample into said tube means inside channel from said tube means outer end, until said tool means extends beyond said tube means outer end, and obtaining said tissue sample with said tool means and removing said tool means from said colon to retrieve said tissue sample.

11. The method of claim 10 further comprising the step of inserting guide wire means into said tube means inside channel to assist in inserting said tube means inner end into said colon.

* * * * *